United States Patent [19]

Logan

[11] Patent Number: 5,511,318
[45] Date of Patent: Apr. 30, 1996

[54] ADJUSTABLE CROSS HAIR ASSEMBLY

[76] Inventor: Davy S. Logan, Post Office Box 116, Orono, Me. 04473

[21] Appl. No.: 333,646

[22] Filed: Nov. 3, 1994

[51] Int. Cl.[6] .................................................. F41G 1/42
[52] U.S. Cl. ..................................................... 33/298
[58] Field of Search ........................... 33/227, 233, 246, 33/265, 286, 297, 298; 356/251, 252; 359/424, 427, 428; 378/205, 206; 124/87

[56] References Cited

U.S. PATENT DOCUMENTS

| | | | |
|---|---|---|---|
| 618,161 | 1/1899 | Brightmore | 33/298 |
| 2,189,766 | 2/1940 | Unertl | 33/298 |
| 2,562,695 | 7/1951 | Brown | 33/297 |
| 2,893,124 | 7/1959 | Sundquist | 33/265 |
| 4,535,544 | 8/1985 | Jones et al. | 33/265 |
| 5,220,907 | 6/1993 | Lonsdale | 33/265 |

FOREIGN PATENT DOCUMENTS 12605  of 1916  United Kingdom ..................... 33/298

Primary Examiner—William A. Cuchlinski, Jr.
Assistant Examiner—G. Bradley Bennett
Attorney, Agent, or Firm—Frederick R. Cantor

[57] ABSTRACT

A cross hair assembly has an adjustable cross hair intersection point to facilitate calibration of the cross hair assembly relative to the optical axis of an associated x-ray radiation source. Each cross hair has a fixed anchorage on a mounting frame, and an adjustable anchorage on the mounting frame. By selectively adjusting the adjustable anchorages it is possible to change the cross hair intersection point. Each cross hair is a steel wire having a relatively small diameter; a coil spring is included in each fixed anchorage for holding the wire in a taut condition free from sagging or bending.

15 Claims, 1 Drawing Sheet

ADJUSTABLE CROSS HAIR ASSEMBLY

BACKGROUND OF THE PRESENT INVENTION

1. Field of the Invention

The present invention relates to a cross hair assembly.

The present invention relates, more particularly, to a cross hair assembly, usable in an X-ray machine, or similar type apparatus, e.g., an accelerator, for aligning a patient's body with a radiation source.

2. Prior Developments

In certain X-ray machines, or accelerators, usable in the medical field, the patient is positioned in a prone position on a table located below the X-ray source; the X-rays are directed downwardly from an overhead source onto the patient's body.

In order to align the specific area of the patient's body that is being treated, or studied, with the X-ray source, a cross hair assembly and light source are used as an alignment tool. The light source is located on the optical axis of the radiation source directly above the cross hair assembly. With the patient most often in a prone position on the table, the light source is energized to direct a concentrated light beam downwardly through the cross hair assembly onto the patient's body. A cross-shaped shadow is cast on the patient's body, designating the area of the body that will receive the X-rays when the X-ray machine is later turned on. The table, or overhead X-ray source, can then be adjusted, as necessary, to move the cross-shaped shadow to the desired point on the patient's body.

One problem with the existing cross hair assemblies is that the intersection point of the cross hairs may not always be in precise optical alignment with the optical axis of the light source or radiation source. Such misalignment can be related to manufacturing tolerances or day-to-day load forces.

Another disadvantage of the existing cross hair assemblies is that the cross hairs are relatively thick, due to the way in which the cross hairs have to be mounted. Each cross hair comprises a steel wire having a diameter of about 0.050 inch, in order to achieve a reasonably rigid taut wire structure free of bends or wrinkles. The large diameter wire tends to cast a relatively wide shadow line on the patient's body.

A further problem associated with conventional cross hair assemblies is that the individual wires (cross hairs) are not easily replaced. Often, when a cross hair breaks, or otherwise becomes non-operational, the entire cross hair assembly has to be replaced.

SUMMARY OF THE PRESENT INVENTION

An object of the present invention is to provide a cross hair assembly.

A further object of the present invention is, more particularly, to provide a cross hair assembly usable in an X-ray machine or similar type apparatus, e.g., an accelerator, for aligning a patient's body with a radiation source.

The present invention is concerned with a cross hair assembly, wherein the individual cross hairs can be adjusted, to vary, or change, the cross hair intersection point, for purposes of calibrating the cross hair assembly to a desired optical alignment with the associated light source.

In preferred practice of the invention each cross hair has one end thereof fixedly anchored to the mounting frame, and the other end adjustably anchored to the mounting frame. A slidable block is connected to said other end of each cross hair, such that manual adjustment of the block along the frame changes the anchorage point of the cross hair. By selectively adjusting the slidable blocks for the respective cross hairs, it is possible to shift the intersection point of the cross hairs, for bringing the cross hair assembly into proper calibration relative to the associated light source.

Each cross hair is preferably a steel wire having a diameter of about 0.025 inch. The relatively small wire diameter is advantageous in that the shadow cast by the wires is relatively thin, whereby the cross hair intersection point is small and well defined on the patient's body.

Each steel wire (cross hair) has a fixed anchorage, defined by a hollow tubular plunger slidably mounted in the mounting frame for limited motion toward or away from the frame central axis; a coil spring encircles each plunger to bias the plunger away from the frame central axis.

The action of each coil spring is such that each associated wire (cross hair) is spring-biased to a straight, taut condition. The tensioned wire is maintained in a straight condition, free of any kinks, wrinkles or droops. The wire can have a relatively small diameter because it does not have to depend on its own rigidity or stiffness in order to be maintained in a straight linear condition. The tension provided by the coil spring, maintains the relatively small diameter wire in a straight linear configuration.

The ends of the steel wires are preferably detachably connected to the fixed anchorages and adjustable anchorages, such that either wire can be replaced by a relatively simple disconnection process. Each adjustable anchorage has a keyhole slot mated to an enlargement on the end of the respective wire (cross hair); the enlargement can be lifted out of the slot manually. Each fixed anchorage comprises a spring-biased tubular plunger that has a cavity or recess in its outer end adapted to receive a relatively large spherical enlargement on the end of the wire; the wire extends through the bore of the tubular plunger. Removal of a cross hair is accomplished by detaching the wire from the keyhole slot in the adjustable anchorage, and pulling the wire through the tubular plunger. The wire-removal process does not require removal of the anchorages from the frame. The anchorages can remain in place on the frame, ready to receive the replacement wire (cross hair).

In summary, and in accordance with the above discussion, the foregoing objectives are achieved in the following embodiments.

1. A cross hair assembly comprising an annular frame;
   a first cross hair extending across said frame, a second cross hair extending across said frame in orthogonal relation to said first cross hair;
   a fixed anchorage on said frame for each cross hair;
   an adjustable anchorage on said frame for each cross hair;
   each said adjustable anchorage comprising a slidable anchorage element slidably mounted on said frame; and
   said adjustable anchorages being independently adjustable to vary the intersection point of the cross hairs.

2. The cross hair assembly, as described in paragraph 1, and further comprising an adjusting screw engageable with each anchorage element, whereby selective rotation of an adjusting screw moves the associated anchorage element along the screw rotational axis.

3. The cross hair assembly, as described in paragraph 2, and further comprising a thumb wheel carried by each adjusting screw for manual rotation of the screw.

4. The cross hair assembly, as described in paragraph 1, wherein each slidable anchorage element comprises a block having a slidable key fit on the frame; and an adjusting screw having threaded engagement with each said block, whereby rotation of a selected screw causes the associated block to slide along the frame.

5. The cross hair assembly, as described in paragraph 4, wherein each adjusting screw extends through the associated block so that opposite ends of the screw are located on opposite sides of the block.

6. The cross hair assembly, as described in paragraph 5, and further comprising two bearings for each adjusting screw, each screw having smooth-surfaced shaft portions extending through the associated bearings.

7. The cross hair assembly, as described in paragraph 6, and further comprising a thumb wheel for each adjusting screw; and each thumb wheel being located on a smooth-surfaced shaft portion of the associated screw.

8. The cross hair assembly, as described in paragraph 7, wherein said frame has a recess therein for receiving each adjustable anchorage; and each adjustable anchorage comprising a unitary sub-assembly that includes a block, an associated screw and two bearings for the screw.

9. The cross hair assembly, as described in paragraph 1, wherein each slidable anchorage element has a detachable connection with the associated cross hair, whereby the cross hair can be disconnected from the associated anchorage element without removing the anchorage element from the frame.

10. The cross hair assembly, as described in paragraph 9, wherein each detachable connection comprises a keyhole slot in the respective block and an enlargement on the cross hair mated to said keyhole slot.

11. The cross hair assembly, as described in paragraph 1, wherein each fixed anchorage comprises an enlargement on the respective cross hair, a tubular plunger having a recess therein for accommodating said enlargement, and spring means biasing the plunger away from the associated adjustable anchorage, whereby the cross hair is in a tensioned condition.

12. The cross hair assembly, as described in paragraph 11, wherein each adjustable anchorage comprises a keyhole slot in the slidable anchorage element, and a second enlargement on the associated cross hair mated to said keyhole slot whereby said second enlargement can be lifted out of the keyhole slot to disconnect the cross hair from the slidable anchorage element.

13. The cross hair assembly, as described in paragraph 12, wherein each tubular plunger has a bore larger than said second enlargement, whereby the respective cross hair can be removed by moving the cross hair through the plunger bore in a direction away from the associated adjustable anchorage.

14. A cross hair assembly comprising an annular frame having a central axis;

a first cross hair extending across said frame, a second cross hair extending across said frame;

said cross hairs having an orthogonal relationship, whereby the cross hairs intersect each other in the vicinity of the frame central axis;

a fixed anchorage on said frame for each cross hair;

each fixed anchorage comprising a first enlargement on the respective cross hair, a tubular plunger having a recess therein for accommodating said first enlargement, and a bore communicating with said recess so that the cross hair extends through the bore;

spring means biasing the plunger away from the frame central axis so that the associated cross hair is in a tensioned condition;

an adjustable anchorage on said frame for each cross hair;

each adjustable anchorage comprising two spaced bearings mounted on the frame, a block slidably mounted on the frame between said bearings, and a rotary screw extending through said block;

each screw having smooth-surfaced shaft portions rotatably mounted in said bearings, whereby rotation of the shaft moves the associated block toward one bearing and away from the other bearing;

each said block having a keyhole slot; and each cross hair having a second enlargement mated to an associated keyhole slot, whereby each cross hair is detachably connected to an associated block.

15. The cross hair assembly, as described in paragraph 14, wherein said first enlargement is larger than said second enlargement, and said second enlargement is smaller than the bore in the associated plunger, such that when a cross hair is disconnected from its associated block it can be removed from the frame by movement through the plunger bore.

A BRIEF DESCRIPTION OF THE DRAWINGS

DESCRIPTION OF THE PREFERRED EMBODIMENTS OF THE PRESENT INVENTION

Figure 1:
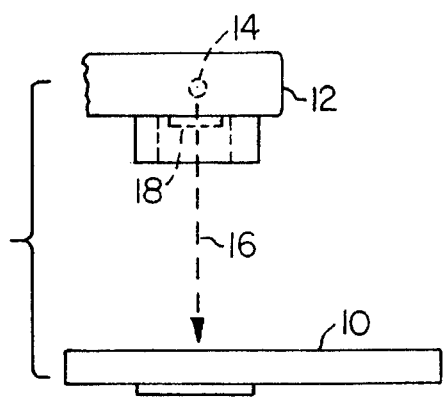
FIG. 1, is a schematic representation, of an X-ray machine suitable for using a cross hair assembly of the present invention.

FIG. 1, is a schematic representation, of an X-ray machine suitable for using a cross hair assembly of the present invention.

FIG. 1, fragmentarily shows an X-ray machine of the type produced by the Siemens Company or by the Varian Company, for medical usage in patient diagnosis or radiation treatment. The machine comprises a horizontal table 10 located below an elevated head, or housing 12, that contains a radiation source; the patient generally lies in a prone position on the table 10, such that the X-rays are directed from the overhead X-ray source downwardly onto the patient's body.

A small high intensity light source 14 is located in housing 12 for directing a beam of light downwardly, as indicated by dashed line 16 in FIG. 1. A cross hair assembly 18 is fastened or mounted to the undersurface of the housing in the path of the light ray generated by light source 14. The light source 14 is located on the optical axis of the X-ray radiation source, so that the path of light ray 16 is representative of the path taken by the X-rays when the radiation source is energized. Light source 14 is used as an alignment tool, prior to actuation of the X-ray source, to ensure that the X-rays will be directed against the desired point on the person's body, i.e., the point requiring diagnosis or treatment.

Light rays passing downwardly through cross hair assembly 18 will cast a shadow on the patient's prone body in a pattern defined by the wires (cress hairs) in assembly 18. The intersection point, i.e., where the wires cross, indicates the target, or area, to be subjected by the X-rays when the radiation source is energized. Table 10 can be adjusted until the pattern of the shadow produced on the patient's body is at the desired location. The X-ray machine is then energized.

Figure 2:
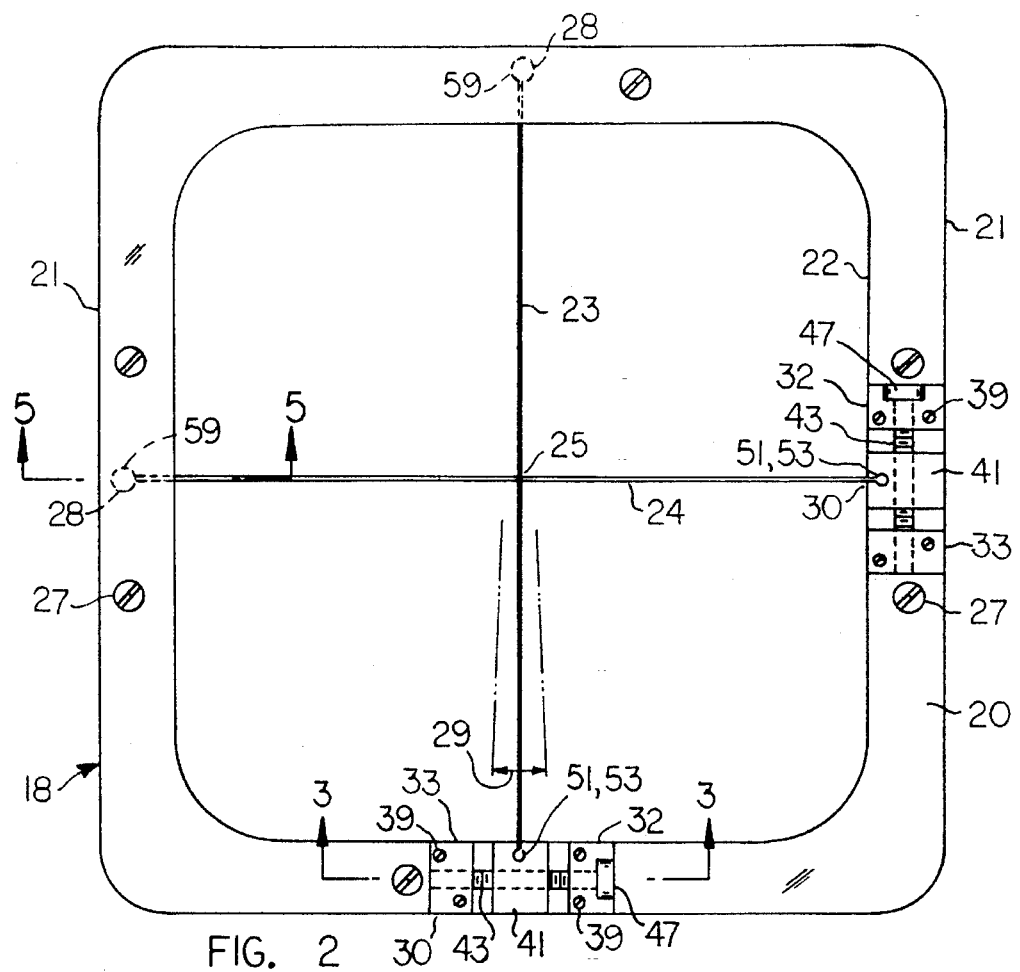
FIG. 2, is a plan view, of a cross hair assembly embodying the present invention.

The present invention is concerned with a specific structural configuration for the cross hair assembly 18 that permits the assembly to be calibrated or adjusted, such that the shadow pattern produced by the cross hair assembly has an intersection point that coincides with the optical axis of the X-ray source. FIG. 2 illustrates a preferred embodiment of the invention.

FIG. 2, is a plan view, of a cross hair assembly embodying the present invention.

As shown in FIG. 2, the cross hair assembly comprises a square annular frame 20 having an outer edge 21 and an inner edge 22. Two cross hairs 23 and 24 extend across the frame 20 at right angles to each other, whereby the cross hairs have an intersection point 25. Each cross hair is preferably a steel wire having a diameter of about 0.025 inch. Frame 20 typically has a dimension along each edge measuring about seven or eight inches. The frame 20 can be attached to a side surface of the X-ray housing by screws 27 extending through holes in the frame into threaded holes in the machine. Frame 20 can be removed from the X-ray machine, but it cannot be shifted or adjusted; it has a fixed location on the machine, dictated by the threaded mounting holes. FIG. 2 is a bottom plan view of the cross hair assembly, looking upwardly toward the undersurface of the X-ray housing and showing the mounting screws 27.

Figure 3:
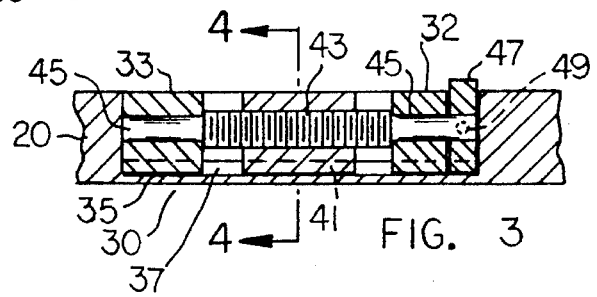
FIG. 3, is an enlarged, fragmentary, cross-sectional view, taken on line 3—3 in FIG. 2.

FIG. 3, is an enlarged fragmentary cross-sectional view, taken on line 3—3 in FIG. 2.

Figure 4:
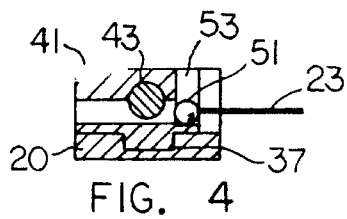
FIG. 4, is a transverse sectional view, taken on line 4—4 in FIG. 3.

FIG. 4, is a transverse sectional view, taken on line 4—4 in FIG. 3.

Figure 5:
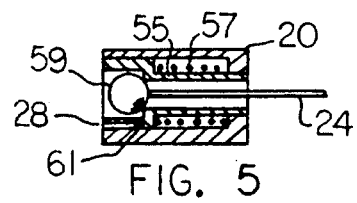
FIG. 5, is an enlarged transverse sectional view, taken on line 5—5 in FIG. 2.

FIG. 5, is an enlarged transverse sectional view, taken on line 5—5 in FIG. 2.

Each cross hair 23 or 24 has one end thereof connected to a fixed anchorage 28, and its other end connected to an adjustable anchorage 30. FIGS. 3 and 4 show the construction of each adjustable anchorage 30. FIG. 5 illustrates the construction of each fixed anchorage 28.

Anchorage 30 is characterized as an adjustable anchorage because it can be manually controlled to vary, or adjust, the location of the cross hair anchorage point, whereby the cross hair position can be changed. In FIG. 2, the limits on the positional change for cross hair 23 are indicated by arrows 29. Similar positional changes are possible for the other cross hair 24.

By changing the cross hair locations it is possible to vary the cross hair intersection point 25, so as to achieve a precise calibrated condition of the cross hair assembly coinciding with the optical axis of the radiation source in the X-ray machine. The ability to calibrate the cross hair assembly is an important feature of the invention.

Referring to FIGS. 2, 3 and 4, each adjustable anchorage 30 comprises two shaft bearings 32 and 33 positioned in an elongated recess 35 in frame 20. The bottom wall of the recess 35 has a groove 37 extending therealong that mates with a central rib or key on the lower face of each bearing 32 or 33, whereby the bearing is presented from lateral displacement relative to frame 20. Each bearing is a rectangular flat-faced bar affixed to frame 20 by two screws 39.

The zone between bearings 32 and 33 is occupied by a slidable block 41, that has a rib or key on its bottom surface mating with groove 37, whereby the block is slidable in the space between the two shaft bearings 32 and 33. A rotary screw 43 extends through a threaded hole in block 41; the screw thread meshes with the hole thread such that rotation of the screw 43 around the screw axis causes the block 41 to move to the left or to the right (in FIG. 3), depending on the direction of the screw rotation.

Opposite end portions of the screw are smooth-surfaced shaft portions 45 rotatably seated in bearings 32 and 33, whereby the screw 43 can rotate but cannot move axially. The right end portion of the screw has a flat surface, so that the shaft portion has a D cross section mated to a D-shaped hole in a thumb wheel 47; a small set screw 49 extends into the thumb wheel 47 to affix the wheel to screw 39.

The assembly, comprising bearings 32 and 33, screw 43 and block 41, is pre-assembled as a unit prior to placement in recess 35 of the frame. Screws 27 hold the assembled unit in place. The thumb wheel 47 has clearance relative to a cavity in the end of bearing 32, such that manual rotation of the thumb wheel moves block 41 along the frame, within the space limitations of bearings 32 and 33.

Each cross hair 23 or 24 has a small spherical enlargement 51 at one end mated to a keyhole slot 53 in a side face of block 41. The spherical enlargement provides a detachable connection between the end of the wire and block 41. The wire can be disconnected from the block by lifting enlargement 51 out of the keyhole slot.

Referring to FIG. 5, there is shown a fixed anchorage 28 for the other end of each wire 23 or 24, i.e., the end of the wire remote from adjustable anchorage 30. The fixed anchorage 28 comprises a tubular plunger 55 slidable in a cylindrical socket in frame 20; a coil spring 57 acts on the head of the plunger 55 to bias the plunger in a leftward direction (as viewed in FIG. 5). The plunger-biasing action of spring 57 is away from the frame central axis as viewed in FIG. 2.

The wire, 23 or 24, has one end thereof connected to a relatively large spherical enlargement 59 that seats within a recess in the head of plunger 55; the wire extends freely through an axial bore in the plunger and across the space circumscribed by frame 20. The opposite end of each wire carries the aforementioned enlargement 51, which is used to detachably connect the wire to block 41.

The biasing action of each coil spring 57 serves to tension the associated wire 23 or 24, whereby the wire is in a linear straight condition, free from droop or bend. The wire diameter can therefore be relatively small, i.e., on the order of 0.025 inch.

The end of each wire connected to anchorage 28 is stationary. The end of each wire attached to block 41 is movable, in accordance with slidable adjustments of the block. Such adjustments are used to change or vary the intersection point 25 of the cross hairs, as necessary to correct for minor errors in the calibration of the cross hair assembly relative to the optical axis of the X-ray tube.

Slidable adjustment of the block 41 associated with cross hair 23 will shift the intersection point 25 laterally, i.e., left or right in FIG. 2. Slidable adjustment of the block 41 associated with cross hair 24 will shift the intersection point 25 vertically, up or down, in FIG. 2. The adjustment capability of blocks 41 constitutes a principal feature of the invention.

A further feature of interest is the connection mechanism used for connecting the ends of each cross hair (wire) to each anchorage 28 or 30. Keyhole slot 53 is designed to permit disconnection of the respective wire from the respective block 41. With enlargement 51 disconnected from the keyhole slot, the wire can be pulled through the associated tubular plunger 55 to completely separate the wire from both anchorages 28 and 30. In this connection, the spherical enlargement 51 has a diameter that is slightly smaller than the bore in plunger 55, such that the small enlargement 51 can pass through the plunger bore.

Typically, each enlargement 51 can have a diameter of about 0.093 inch; the plunger bore diameter can be 0.093 inch or greater, whereby the enlargement 51 can slide through the bore.

Removal and replacement of each cross hair can be achieved without removing or disturbing anchorages 28 and 30. A small drive pin 61 can be incorporated into anchorage 28 to prevent separation of plunger 55 from frame 20. Plunger 55 has a flat slidable surface on pin 61, whereby the plunger can slide back and forth within its mounting socket, without fear that the plunger might slip out of the socket.

The present invention described above, relates to an Adjustable Cross Hair Assembly. Features of the present invention are recited in the appended claims. The drawings contained herein necessarily depict structural features and embodiments of the Adjustable Cross Hair Assembly, useful in the practice of the present invention.

However, it will be appreciated by those skilled in the arts pertaining thereto, that the present invention can be practiced in various alternate forms and configurations. Further, the previous detailed descriptions of the preferred embodiments of the present invention are presented for purpose of clarity of understanding only, and no unnecessary limitations should be implied therefrom. Finally, all appropriate mechanical and functional equivalents to the above, which may be obvious to those skilled in the arts pertaining thereto, are considered to be encompassed within the claims of the present invention.

What is claimed is:

1. A cross hair assembly comprising an annular frame;

a first cross hair extending across said frame, a second cross hair extending across said frame in orthogonal relation to said first cross hair;

a fixed anchorage on said frame for each cross hair;

an adjustable anchorage on said frame for each cross hair;

each cross hair having a first end connected to the associated fixed anchorage, and a second end connected to the associated adjustable anchorage;

each said adjustable anchorage comprising a slidable anchorage element slidably mounted on said frame for adjusting movements normal to the direction taken by the associated cross hair; and said adjustable anchorages being independently adjustable to vary the intersection point of the cross hairs.

2. The cross hair assembly, as described in claim 1, wherein each adjustable anchorage further comprises an adjusting screw engageable with each anchorage element, whereby selective rotation of an adjusting screw moves the associated anchorage element along the screw rotational axis.

3. The cross hair assembly, as described in claim 2, wherein each adjustable anchorage further comprises a thumb wheel carried by each said adjusting screw for manual rotation of the screw.

4. The cross hair assembly, as described in claim 1, wherein each slidable anchorage element comprises a block having a slidable key fit on the frame; each adjustable anchorage further comprising an adjusting screw having threaded engagement with each said block, whereby rotation of a selected screw causes the associated block to slide along the frame.

5. The cross hair assembly, as described in claim 4, wherein each adjusting screw extends through the associated block so that opposite ends of the screw are located on opposite sides of the block.

6. The cross hair assembly, as described in claim 5, wherein each adjustable anchorage further comprises two bearings for each adjusting screw, each screw having smooth-surfaced shaft portions extending through the associated bearings.

7. The cross hair assembly, as described in claim 6, wherein each adjustable anchorage further comprises a thumb wheel for each associated adjusting screw; each thumb wheel being located on a smooth-surfaced shaft portion of the associated screw.

8. The cross hair assembly, as described in claim 7, wherein said frame has a recess therein for receiving each adjustable anchorage; and each adjustable anchorage comprising a unitary sub-assembly installable as a unit in one of the recesses in said frame.

9. The cross hair assembly, as described in claim 1, wherein each slidable anchorage element has a detachable connection with the associated cross hair, whereby the cross hair can be disconnected from the associated slidable anchorage element without removing said slidable anchorage element from the frame.

10. The cross hair assembly, as described in claim 9, wherein each detachable connection comprises a keyhole slot in the respective block and an enlargement on said second end of the respective cross hair, each said enlargement being mated to the associated keyhole slot so as to be liftable out of the slot.

11. The cross hair assembly, as described in claim 1, wherein each fixed anchorage comprises an enlargement on the first end of the respective cross hair, a tubular plunger having a recess therein for accommodating said enlargement, and spring means biasing the plunger away from the associated adjustable anchorage, whereby the cross hair is in a tensioned condition.

12. The cross hair assembly, as described in claim 11, wherein each adjustable anchorage comprises a keyhole slot in the slidable anchorage element, and a second enlargement on the second end of the associated cross hair mated to said keyhole slot, whereby said second enlargement can be lifted out of the keyhole slot to disconnect the cross hair from the slidable anchorage element.

13. The cross hair assembly, as described in claim 12, wherein each tubular plunger has a bore larger than said second enlargement, whereby the respective cross hair can be removed by moving the cross hair through the plunger bore in a direction away from the associated adjustable anchorage.

14. A cross hair assembly comprising an annular frame having a central axis;

a first cross hair extending across said frame, a second cross hair extending across said frame;

said cross hairs having an orthogonal relationship, whereby the cross hairs intersect each other in the vicinity of the frame central axis;

each cross hair having a first end and a second end;

a fixed anchorage on said frame for each cross hair;

each fixed anchorage comprising a first enlargement on the first end of the respective cross hair, a tubular plunger having a recess therein for accommodating said first enlargement, a bore communicating with said recess so that the cross hair extends through the bore, and spring means biasing said plunger away from the frame central axis so that the associated cross hair is in a tensioned condition;

an adjustable anchorage on said frame for each cross hair;

each adjustable anchorage comprising two spaced bearings mounted on the frame, a block slidably mounted on the frame between said bearings, and a rotary screw extending through said block;

each screw having smooth-surfaced shaft portions rotatably mounted in said bearings, whereby rotation of the shaft moves the associated block toward one bearing and away from the other bearing;

each said block having a keyhole slot; and a second enlargement on the second end of each cross hair mated to an associated keyhole slot, whereby each cross hair is detachably connected to an associated block.

15. The cross hair assembly, as described in claim 14, wherein each said first enlargement is larger than the associated second enlargement, and each said second enlargement is smaller than the bore in the associated plunger, such that when a cross hair is disconnected from its associated block it can be removed from the frame by movement through the plunger bore.

* * * * *